United States Patent
Matsumoto et al.

[11] Patent Number: 5,961,799
[45] Date of Patent: Oct. 5, 1999

[54] COMPACT APPARATUS FOR MEASURING A LIQUID COMPONENT IN A LIQUID SAMPLE

[75] Inventors: Toru Matsumoto; Hidetaka Fujiwara, both of Tokyo, Japan

[73] Assignee: NEC Corporation, Tokyo, Japan

[21] Appl. No.: 08/922,674

[22] Filed: Sep. 3, 1997

[30] Foreign Application Priority Data

Sep. 3, 1996 [JP] Japan .................................. 8-233120

[51] Int. Cl.⁶ .................................................. G01N 27/26
[52] U.S. Cl. ............................ 204/400; 422/102; 422/104
[58] Field of Search .................................. 204/409, 403, 204/400, 279; 73/61.59, 64.56; 422/102, 104

[56] References Cited

U.S. PATENT DOCUMENTS

| | | | |
|---|---|---|---|
| 3,701,716 | 10/1972 | Deuringer et al. | 204/409 |
| 4,073,713 | 2/1978 | Newman | 204/403 |
| 4,894,137 | 1/1990 | Takizawa et al. | 204/403 |
| 5,264,103 | 11/1993 | Yoshioka et al. | 204/403 |
| 5,429,726 | 7/1995 | Johnson et al. | |
| 5,507,935 | 4/1996 | Coleman et al. | 204/409 |
| 5,651,869 | 7/1997 | Yoshioka et al. | 204/403 |

FOREIGN PATENT DOCUMENTS

| | | |
|---|---|---|
| 49-82784 | 11/1972 | Japan . |
| 3-273153 | 12/1991 | Japan . |
| 1281988 A1 | 1/1987 | U.S.S.R. .............................. 204/403 |

*Primary Examiner*—Robert Warden
*Assistant Examiner*—Andrew Aldag
*Attorney, Agent, or Firm*—Sughrue, Mion, Zinn, Macpeak & Seas, PLLC

[57] ABSTRACT

In a liquid component measuring apparatus including a measuring cell (11) which measures a specific component of a predetermined amount of liquid sample by diluting, as diluted liquid sample, the predetermined amount of liquid sample with a buffer solution having a pH buffer capacity and a support electrolyte, the measuring cell includes a metering section (12) having an upper part tapered upward and having a metering space therein. A sample injection port (19) is formed at a top of the upper part. A buffer injection port (18) supplies the buffer solution to the metering space so that the metering space is completely filled with the buffer solution. Disposed around the metering section, a reservoir (13) temporarily reserves, as a reserved buffer solution, the buffer solution which overflows from the sample injection port when the buffer solution is supplied to the metering space by the buffer injection port to be completely filled into the metering space and when the predetermined amount of liquid sample is introduced into the metering space from the buffer injection port so that the metering space is filled with the diluted liquid sample. Disposed in the metering space, a stirrer (17) stirs the diluted liquid sample. Disposed in the metering space, a sensor (15) senses the specific component in the diluted liquid sample. A buffer discharge port (14) discharges the reserved buffer solution from the reservoir into outside of the measuring cell.

10 Claims, 6 Drawing Sheets

COMPACT APPARATUS FOR MEASURING A LIQUID COMPONENT IN A LIQUID SAMPLE

BACKGROUND OF THE INVENTION

This invention relates to a liquid component measuring apparatus for measuring a specific component in a liquid sample.

As disclosed in Japanese Unexamined Patent Publication (JP-A) No. 3-273153 (273153/1991), a conventional liquid component measuring apparatus of the type is used in a clinical test in successively and easily measuring a specific component of, for example, glucose or urea contained in a liquid sample of, for example, body fluid with high accuracy. The body fluid is exudation fluid obtained by removing blood and horny layers from skin and by subjecting the skin to a suction processing under a reduced pressure so that the exudation fluid is exuded from the skin.

Figure 1:
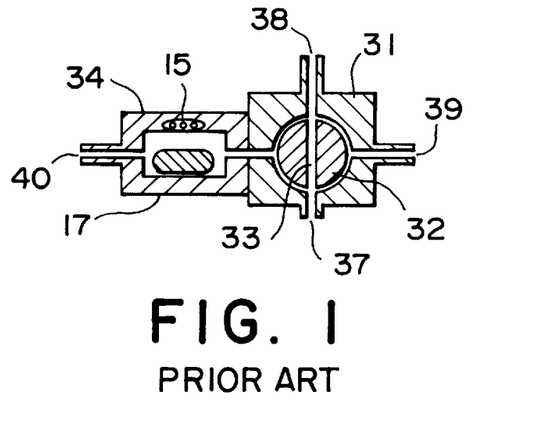
FIG. 1 is a sectional view of a conventional liquid component measuring apparatus.

Referring to FIG. 1, the conventional liquid component measuring apparatus comprises a housing 31 and a cell 34 coupled thereto. The housing 31 is provided with a sampling port 37, a suction port 38, and a diluting liquid introducing port 39. Within the housing 31, a valve 32 having a through hole 33 is arranged to be rotatable. When the valve 32 is rotated to a position illustrated in the figure, the through hole 33 is aligned with the sampling port 37 and the suction port 38 to define a sampling path or channel for the liquid sample. The through hole 33 also serves as a liquid sample storage chamber storing a predetermined amount of the liquid sample. On the other hand, when the valve 32 is rotated to another position, the through hole 33 communicates with the diluting liquid introducing port 39 and an internal cavity of the cell 34. The cell 34 is provided inside with a stirrer 17 and a sensor 15 and has a discharge port 40.

Referring to FIGS. 2A through 2D, operation of the conventional liquid component measuring apparatus will be described in conjunction with measurement of glucose concentration in the body fluid exuded as the exudation fluid. For clarity of illustration, only the body fluid, the diluting liquid, and the body fluid after diluted are shown as hatched portions.

Figure 2A:
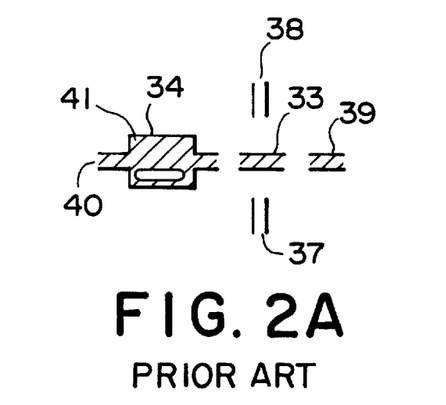
FIGS. 2A through 2D are views for describing operation of the conventional liquid component measuring apparatus illustrated in FIG. 1.

At first referring to FIG. 2A, the valve 32 (FIG. 1) is kept at an initial position where the through hole 33 extends in a horizontal direction and communicates with the diluting liquid introducing port 39 and the interior of the cell 34. The diluting liquid depicted at 41, for example, an HEPES buffer solution of 20 mM and pH 7.5 is introduced through the diluting liquid introducing port 39 to fill the through hole 33 of the valve 32 and the interior of the cell 34.

Figure 2B:
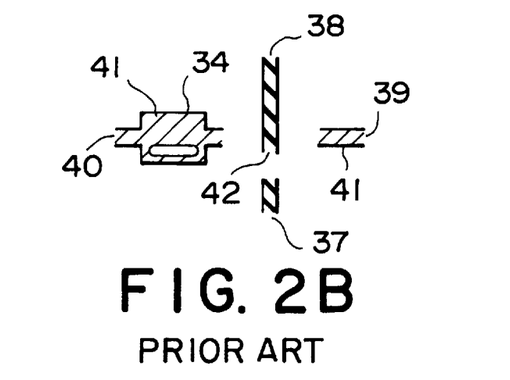

Next referring to FIG. 2B, the valve 32 is rotated by 90° to align the through hole 33 with the sampling port 37 and the suction port 38 so that the sampling path is formed. Then, the through hole 33 is filled with the body fluid 42.

Figure 2C:
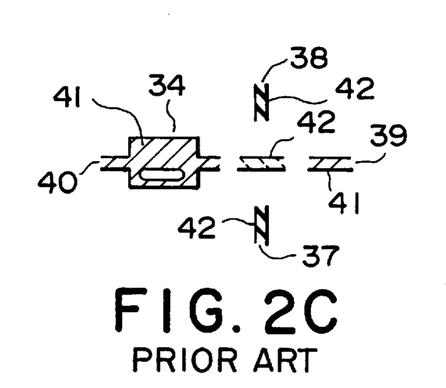
Figure 2D:
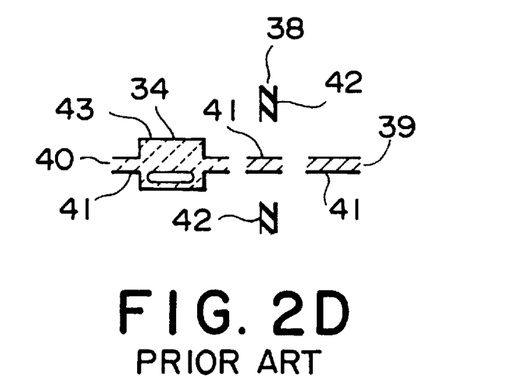

Turning to FIG. 2C, the valve 32 is rotated by 90° to return to the initial position where the through hole 33 communicates with the diluting liquid introducing port 39. Then, the diluting liquid 41 is fed through the diluting liquid introducing port 39 to extrude the body fluid 42 filled in the through hole 33 to the interior of the cell 34. Within the cell 34, the body fluid 42 is stirred by the stirrer 17 and diluted by the diluting liquid 41, as illustrated in FIG. 2D. The glucose concentration is measured by a glucose sensor arranged in the cell 34.

At this time, a dilution ratio of the body fluid is exactly determined by the ratio between the volume of the through hole 33 of the valve 32 and the effective volume of the cell 34 so that the dilution is carried out with high accuracy. Generally, the body fluid does not have a constant pH or a constant pH buffer capacity. However, by the use of a pH buffer solution constant in pH, pH buffer capacity, and ionic strength and sufficient in oxygen/enzyme concentration as the diluting liquid, it is possible to control the pH, the pH buffer capacity, the ionic strength, and the oxygen/enzyme concentration of the liquid sample to be measured. Thus, the measurement is carried out with high accuracy.

In order to calibrate the sensor, the cell 34 may further be provided with another inlet port for a reference liquid having a known component. The above-mentioned apparatus can be applied not only to the exuded fluid and the blood but also to various other liquids. The sensor may be selected from various types in correspondence to the liquid sample to be measured.

Another conventional liquid component measuring apparatus of the type is disclosed in U.S. Pat. No. 5,429,726. This apparatus is used to successively and easily measure the amount of L-Asp-L-Phe-methyl ester in soft drinks with high accuracy.

Figure 3:
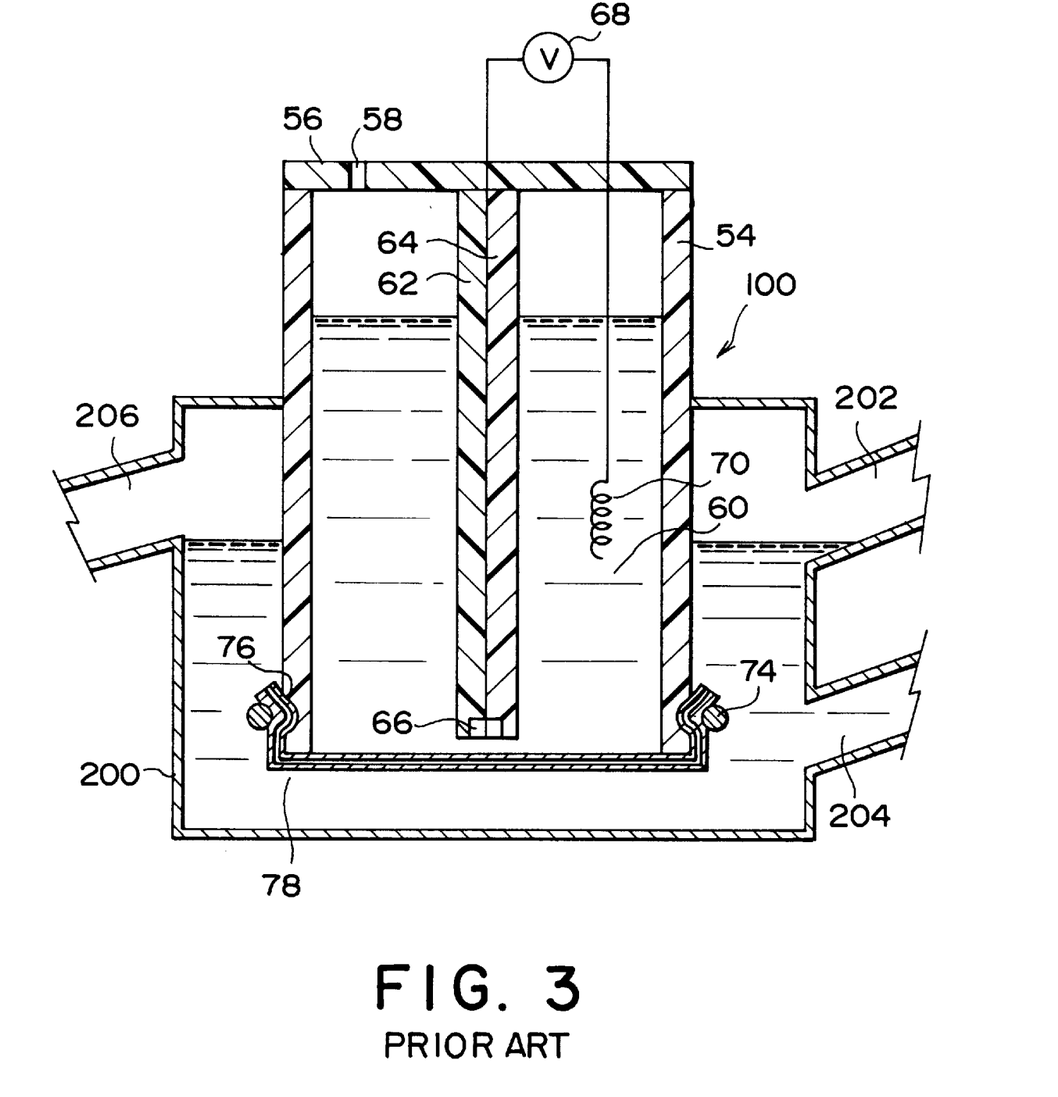
FIG. 3 is a sectional view of another conventional liquid component measuring apparatus.

Referring to FIG. 3, the liquid component measuring apparatus disclosed in the above-mentioned United States patent comprises a polarographic cell 100 including an electrically insulating container 54 composed of a suitable dielectric material, such as glass or plastic. The container 54 is covered by an electrically insulating cap 56. The cap 56 is provided with an aperture 58 through which an electrolyte 60 is admitted to the cell 100. An electrically insulating rod or column 62 extending from the cap 56 downwardly into the cell 100 is provided with a conductor 64. The conductor 64 is connected at the distal end thereof to a working or sensor electrode 66 which may be composed of platinum, gold, silver, graphite, or the like. The proximal end of the conductor 64 is connected with a DC voltage source 68.

A reference electrode 70 is provided between the column 62 and the walls of the container 54. The reference electrode 70 may comprise a silver chloride coated silver wire. The electrolyte 60 fills the space between the reference electrode 70 and the working electrode 66.

The lower end of the container 54 is provided with an O-ring 74 snap fit into an annular groove 76 on the outer wall of the container 54 to hold a laminated enzyme-containing membrane 78 securely in fluid tight relation over the bottom of the container 54.

Surrounding the bottom portion of the polarographic cell 100 is a reservoir 200 adapted to contain an analyte containing solution or buffer. The reservoir 200 includes an analyte injection channel 202 and a buffer injection channel 204. An overflow weir 206 provides for overflow to drain from the apparatus.

The first-mentioned conventional apparatus requires a high-accuracy metering pump as the feeding pump and the valve for switching a fluid path or channel alternately to feed the diluting liquid and to introduce the liquid sample. Therefore, the apparatus inevitably becomes bulky in size. This results in restriction in portability and measuring site.

In addition, the housing is provided with the valve, a motor for driving the valve, the through hole, the sampling port, the diluting liquid introducing port, and the suction port while the cell is provided with the sensor, the stirrer, and the discharge port. Thus, the first-mentioned apparatus requires a number of components and is therefore complicated in structure.

In the second-mentioned conventional apparatus, the sensor is incorporated into an electrochemical reactor chamber.

In order to exchange the sensor, at least a part of the electrochemical reactor chamber must be disassembled. Thus, exchange of the sensor is troublesome and inconvenient.

The liquid sample to be measured by the apparatus often contains foreign particles or impurities, for example, coagulated and deposited protein and bubbles. In this event, the dilution ratio may become inaccurate and the interior of the cell can not sufficiently be cleaned. In this case, the accuracy of measurement will be degraded for some types of the samples.

In addition, since the liquid component measuring apparatus comprises a number of components and is therefore complicated in structure as described above, a production cost will be increased owing to such complicated structure.

SUMMARY OF THE INVENTION

It is an object of this invention to provide a liquid component measuring apparatus which has a simplified structure for diluting and measuring a liquid sample and is therefore reduced in size.

It is another object of this invention to provide a liquid component measuring apparatus which is improved in accuracy so as to measure a liquid component in a trace liquid sample.

It is still another object of this invention to provide a liquid component measuring apparatus which allows a sensor to be easily exchanged.

It is a yet another object of this invention to provide a liquid component measuring apparatus which is Improved in productivity.

According to this invention, there is provided a liquid component measuring apparatus comprising a measuring cell which measures a specific component of a predetermined amount of liquid sample by diluting, as diluted liquid sample, the predetermined amount of liquid sample with a buffer solution having a pH buffer capacity and a support electrolyte. The measuring cell comprises: a metering section having an upper part tapered upward and having a metering space therein; a sample injection port formed at a top of the upper part; a buffer injection port coupled to the metering section for supplying the buffer solution to the metering space so that the metering space is completely filled with the buffer solution; a reservoir disposed around the metering section for temporarily reserving, as a reserved buffer solution, the buffer solution which overflows from the sample injection port when the buffer solution is supplied to the metering space by the buffer injection port to be completely filled into the metering space and when the predetermined amount of liquid sample is introduced into the metering space from the buffer injection port so that the metering space is filled with the diluted liquid sample; a stirrer disposed in the metering space for stirring the diluted liquid sample; a sensor disposed in the metering space for sensing the specific component in the diluted liquid sample; and a buffer discharge port coupled to the reservoir for discharging the reserved buffer solution from the reservoir into outside of the measuring cell.

Preferably, the upper part of the metering section has a conical outer surface.

In this case, the conical outer surface of the upper part of the metering section preferably has an inclination angle between 60° and 120°.

Preferably, at least a portion of the metering section that is brought into contact with the buffer solution and the diluted liquid sample is composed of a material selected from the group consisting of metal oxide, anti-corrosion metal, and hydrophobic macromolecule.

Alternatively, at least a portion of the metering section that is brought into contact with the buffer solution and the diluted liquid sample is composed of stainless steel.

Preferably, at least a portion of the metering section that is brought into contact with the buffer solution and the diluted liquid sample is composed of a material selected from the group consisting of fluorine macromolecule and polyalkylsiloxane.

Alternatively, at least a portion of the metering section that is brought into contact with the buffer solution and the diluted liquid sample has a first part composed of stainless steel and a second part composed of a material selected from the group consisting of fluorine macromolecule and polyalkylsiloxane.

Preferably, the sensor is mounted through an O-ring over a bottom of the metering section.

Preferably, the sensor comprises a working electrode, and a counter electrode formed on an insulating support substrate, an enzyme membrane formed on the working and the counter electrodes, and a resin layer surrounding the enzyme membrane.

Preferably, the apparatus further comprises a single pump for feeding the buffer solution to the buffer injection port and for discharging the reserved buffer solution from the reservoir into the outside of the measuring cell.

In the above-mentioned apparatus, the upper part of the metering section of the measuring cell is tapered upward. The sample injection port is formed at the top of the upper part of the metering section. With this structure, it is possible, without using a high-accuracy metering pump as a feed pump, to automatically and easily carry out metering of the buffer solution and cleaning of the metering section of the measuring cell. By mounting the sensor through the O-ring over the bottom of the metering section of the measuring cell, the number of parts of the measuring cell can be reduced. Since the interior of the cell has a simple structure, the measuring cell can be easily exchanged. Even if foreign particles or impurities are mixed in the liquid sample to be measured, such admixed substance can be quickly expelled to the reservoir or a waste tank.

DESCRIPTION OF THE PREFERRED EMBODIMENTS

Now, description will be made about a first embodiment of this invention with reference to the drawing.

Figure 4:
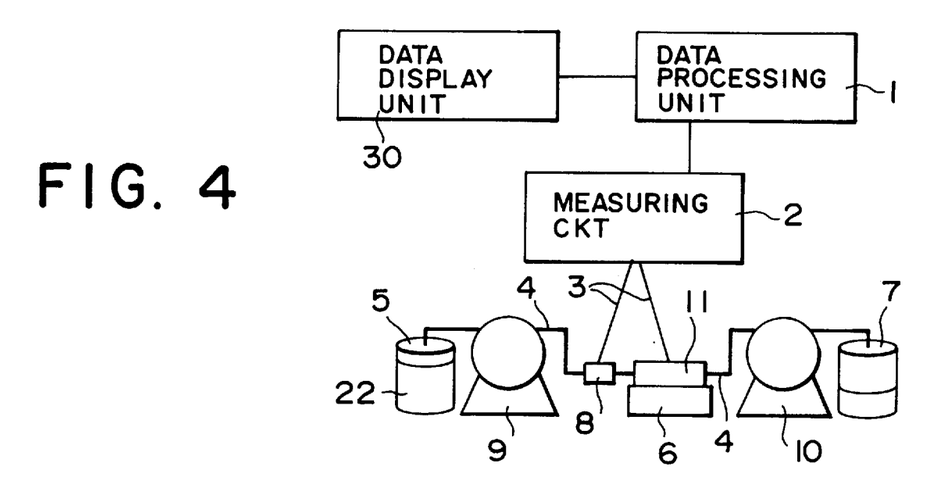
FIG. 4 is a schematic diagram of a liquid component measuring apparatus according to a first embodiment of this invention.

Referring to FIG. 4, a liquid component measuring apparatus according to this invention comprises a measuring cell 11 which will later be described in detail, a measuring circuit 2 connected to the measuring cell 11, a data processing unit 1 connected to the measuring circuit 2 for processing a measurement result signal into numerical data, a data display unit 30 connected to the data processing unit 1 for displaying the numerical data, a reference electrode B for use in electrochemical measurement, a stirring unit 6 coupled to the measuring cell 11, and lead wires 3 connecting the reference electrode 8, the measuring cell 11, the measuring circuit 2, the data processing unit 1, and the data display unit 30 in the manner illustrated in the figure. The liquid component measuring apparatus further comprises a buffer tank 5 storing a buffer solution 22, a waste tank 7 storing a waste liquid including the buffer solution 22 and a liquid sample after measurement, a feeding pump 9 for feeding the buffer solution 22 from the buffer tank 5 into the measuring cell 11, a discharge pump 10 for discharging the buffer solution 22 from the measuring cell 11 into the waste tank 7, and a tube 4 connecting the buffer tank 5, the feeding pump 9, the discharge pump 10, and the waste tank 7 in the manner illustrated in the figure.

The feeding pump 9 and the discharge pump 10 may be of any type as far as the tube 4 can be connected thereto. Alternatively, a squeezing pump such as a pelistaltic pump may be used. The measuring cell 11 communicates through the tube 4 with the buffer tank 5, the feeding pump 9, the discharge pump 10, and the waste tank 7. For example, when lactic acid in the liquid sample is to be measured, the buffer solution 22 may be 0.01–1M N-trismethyl-2-aminoethanesulfonic acid containing 0.01–0.5M sodium sulfate or sodium chloride of a pH adjusted between 6 and 8.

Figure 5A:
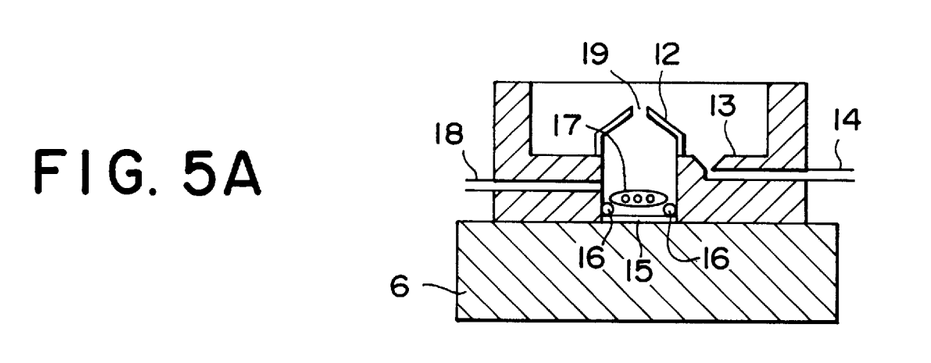
FIGS. 5A and 5B are a sectional view and a plan view of a measuring cell illustrated in FIG. 4, respectively.
Figure 5B:
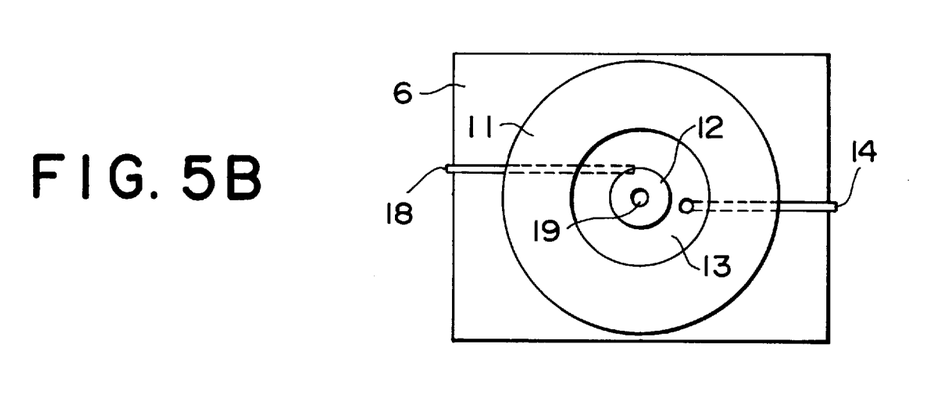

Referring to FIGS. 5A and 5B, the measuring cell 11 comprises a stirrer 17 rotated by the stirring unit 6, a metering section 12 supplied with a liquid sample through a sample injection port 19 and metering the buffer solution 22 supplied through a buffer injection port 18, a reservoir 13 for temporarily storing the buffer solution 22 overflowing from the metering section 12 before it is discharged through a buffer discharge port 14, a sensor 15, and an O-ring 16 for tightly attaching the sensor 15 over the bottom of the metering section 12. The buffer solution 22 successively flows through the buffer injection port 18, the metering section 12, the sample injection port 19, the reservoir 13, and the buffer discharge port 14 in this order.

The sensor 15 may be of any type based on a hydrogen peroxide detection system in which hydrogen peroxide is produced by a catalytic reaction. An enzyme electrode may be composed of lactic acid, glucose, galactose, lactose, sucrose, ethanol, methanol, starch, uric acid, pyruvic acid, amino acid, monoamine, cholesterol, choline, and so on. The sensor 15 mounted on the measuring cell 11 comprises a working electrode and a counter electrode composed of platinum, gold, silver, carbon, and the like.

As illustrated in FIG. 5A, the metering section 12 has an upper part which is tapered upward and has a metering space therein. The upper part has a conical outer surface having an inclination angle between 0° and 180° (both exclusive), preferably, between 60° and 120° (both inclusive). The sample injection port 19 is formed or arranged at the top of the upper part of the metering section 12 and serves to allow injection of the liquid sample and to measure the buffer solution 22 in the metering section 12. When the buffer solution 22 is supplied over a predetermined amount, the metering section 12 quickly discharges an excess amount of the buffer solution 22 through the sample injection port 19. The metering section 12 is made of a material selected from metal oxide, anti-corrosion metal having a high corrosion resistance against the buffer solution 22 and the liquid sample to be measured, and hydrophobic macromolecule. Alternatively, the surface of the metering section 12 may be subjected to hydrophobic treatment. Specifically, stainless steel such as SUS304, fluorine macromolecule such as polytetrafluoroethylene, and polyalkylsiloxane such as dimethylpolysiloxane are desirable. The stirrer 17 is preferably made of a hydrophobic material or a material with its surface subjected to hydrophobic treatment. Specifically, fluorine macromolecule such as polytetrafluoroethylene or a material treated by polyalkylsiloxane such as dimethyl(poly)siloxane. The buffer injection port 18, the buffer discharge port 14, and the reservoir 13 may be formed by thermoplastic resin such as vinyl chloride resin, acrylic resin, and ABS resin, thermosetting resin, silicon, or a metal material.

As seen from FIGS. 5A and 5B, the buffer solution 22 successively flows through the buffer injection port 18, the metering section 12, the sample injection port 19, the reservoir 13, and the buffer discharge port 14 in this order. The sensor 15 is mounted through the O-ring 16 on the measuring cell 11 between the metering section 12 and the stirring unit 6.

Referring to FIGS. 6A through 6E and 7 in addition, operation of this embodiment will be described.

Figure 6A:
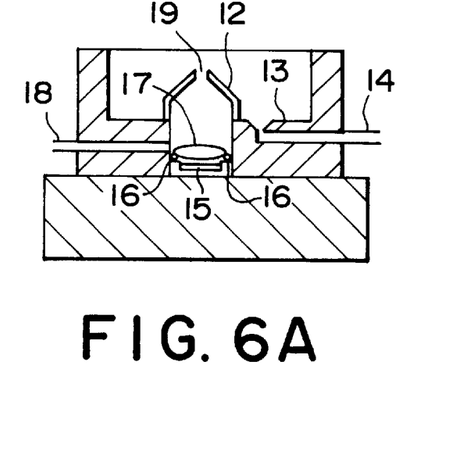
FIGS. 6A through 6E are views for describing the flow of a buffer solution through the measuring cell illustrated in FIG. 4.

At first referring to FIG. 6A, the measuring cell 11 is in an initial state in which the stirrer 17 is stopped.

Figure 6B:
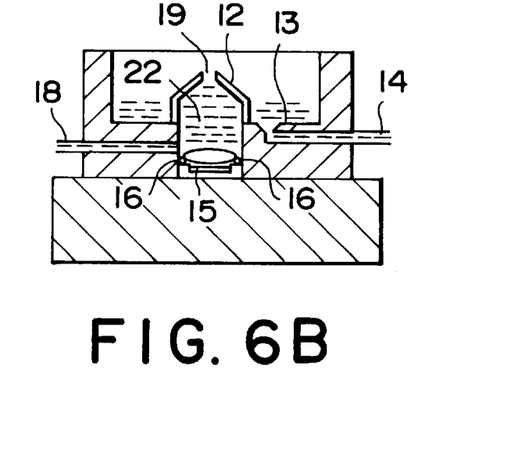

Referring to FIG. 6B, the feeding pump 9 is operated to inject the buffer solution 22 stored in the buffer tank 5 successively into the tube 4, the buffer injection port 18, and the metering section 12. When the buffer solution 22 overflows through the sample injection port 19, the feeding pump 9 is stopped. At this time, the metering space of the metering section 12 is completely filled with a predetermined amount of the buffer solution 22. For example, it is assumed that the metering space of the metering section 12 has a volume of 100 µl. In this event, in order to completely fill the metering space of the metering section 12 with the buffer solution 22 with impurities and bubbles removed, an optimum feeding rate ranges between 0.05 and 0.5 ml/s and an optimum flow rate is equal to 0.1 ml/s. A feeding time is between 1 and 10 seconds, preferably, 4 seconds. The excess amount of the buffer solution 22 is quickly discharged through the sample injection port 19 to be temporarily reserved in the reservoir 13. At this time, the stirrer 17 is stopped or rotated. As described above, the sample injection port 19 not only serves to allow injection of the liquid sample but also to meter the buffer solution 22.

Figure 6C:
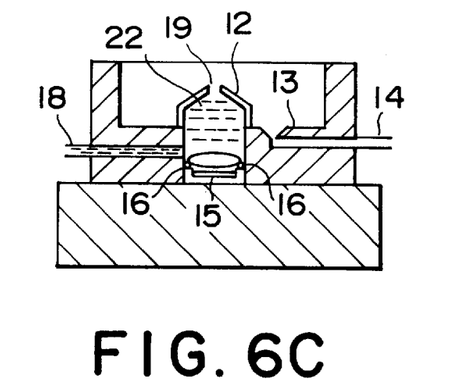

Referring to FIG. 6C, a measuring operation is carried out. While the rotator 17 is rotated, the measuring circuit 2 applies the working electrode of the sensor 15 with a voltage between 0.5 and 0.9 V, preferably, 0.7V with respect to the reference electrode 8. The liquid sample of a volume between 2 and 10 µl, preferably, 4 µl is injected through the sample injection port 19 into the metering space of the metering section 12 by the use of a pipet or a syringe. The measuring circuit 2 measures a current value obtained at the working electrode of the sensor 15. Supplied with the current value thus obtained, the data processing unit 1 analyzes a specific component and produces an analyzed value which is displayed by the data display unit 30. Simultaneously, the discharge pump 10 is operated to discharge the buffer solution 22 from the reservoir 13.

Figure 6D:
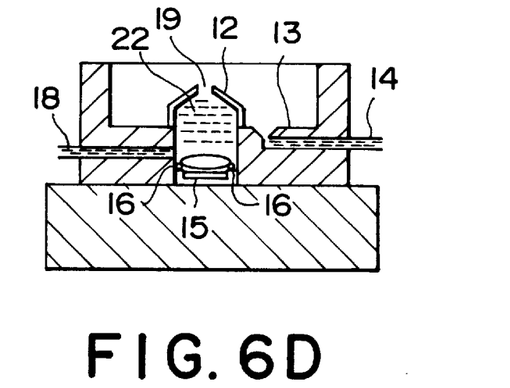

Referring to FIG. 6D, the feeding pump 9 and the discharge pump 10 are operated for at least 4 seconds to inject the buffer solution 22 into the metering section. As a result, the buffer solution 22 containing the liquid sample after measurement overflows through the sample injection port 19 to the reservoir 13. The buffer solution 22 containing the liquid sample after measurement is discharged through the tube 4 into the waste tank 7. The stirrer 17 is stopped or rotated.

Figure 6E:
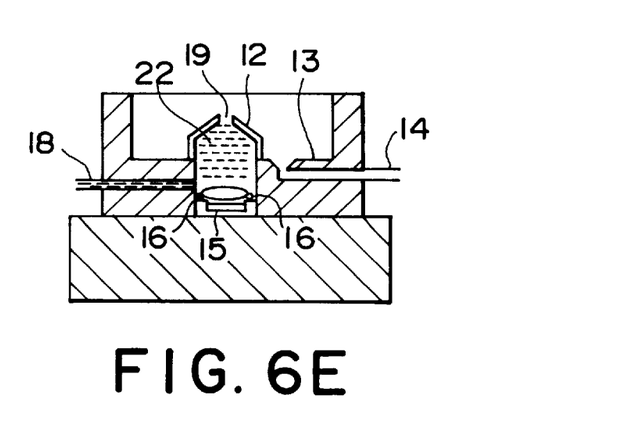

Referring to FIG. 6E, the measuring cell 11 is ready for next measurement. The stirrer 17 is stopped. Then, the similar operation to that mentioned in conjunction with FIGS. 6C through 6E is repeated.

Figure 7:
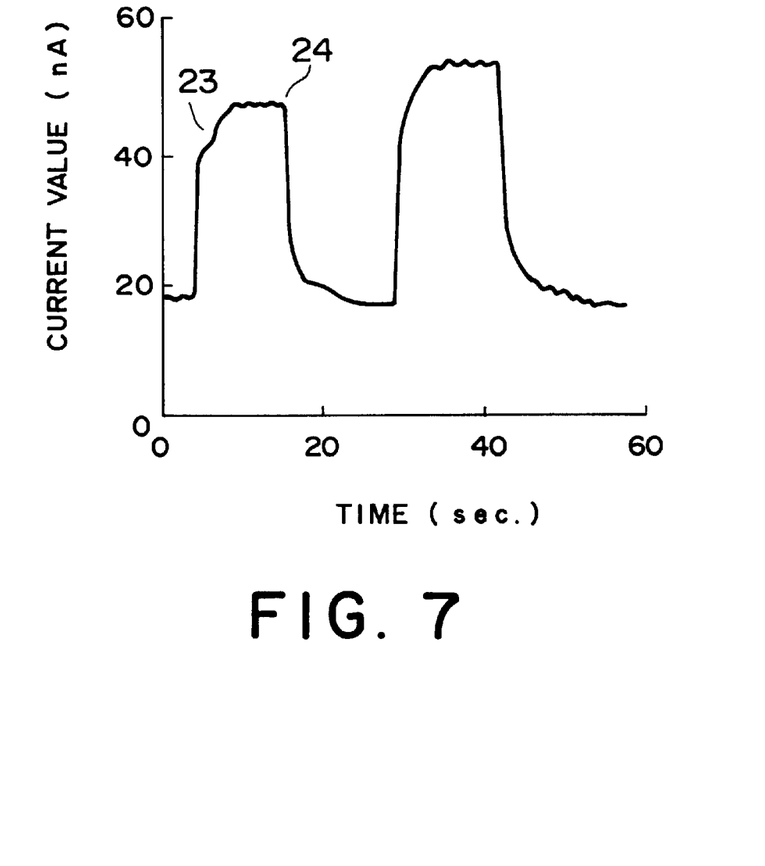
FIG. 7 is a graph showing a sensor output characteristic observed in actual measurement performed by the liquid component measuring apparatus illustrated in FIG. 4.

Referring to FIG. 7, a sensor output characteristic is plotted as a result of actual measurement when the feeding pump 9 and the discharge pump 10 are operated for four seconds to inject and discharge the buffer solution 22. As will be understood from the figure, the sensor output is stabilized after lapse of 5 seconds from a time instant 23 of injection of the liquid sample. After lapse of 15 seconds from a time instant 24 of operation the pumps 9 and 10, the next measurement is allowed.

As described above, the measurement and the cleaning can be repeatedly carried out.

Next, specific examples of this invention will be described.

EXAMPLE 1

The sensor for detecting lactic acid and glucose was mounted on the measuring cell. The liquid sample of 4 $\mu$l was injected into the metering section having a volume of 100 $\mu$l. The feeding pump was operated for 4 seconds (feeding rate of 0.1 ml/s). In this condition, lactic acid and glucose in a serum sample were measured. As a result, reproducibility after repetition is obtained as shown in Table 1.

TABLE 1

Reproducibility in Measurement of
Lactic Acid and Glucose in Serum Sample

| Component | Reproducibility |
| --- | --- |
| Lactic Acid | 1.9% |
| Glucose | 2.2% |

Herein, the reproducibility after repetition is calculated in the following manner. The same serum sample was repeatedly subjected to measurement fifteen times to obtain measurement values. The standard deviation of the measurement values is divided by an average value to obtain a quotient. The quotient is multiplied by 100 to obtain a product as the reproducibility.

EXAMPLE 2

The sensor for detecting lactic acid was mounted on the measuring cell. The liquid sample of 4 $\mu$l was injected into the metering section having a volume of 100 $\mu$l. The feeding pump was operated for 4 seconds (or 10 seconds) (feeding rate of 0.1 ml/s). In this condition, lactic acid in the serum sample was repeatedly measured fifteen times. As a result, reproducibility after repetition is obtained as shown in Table 2.

TABLE 2

Reproducibility in Measurement of
Lactic Acid in Serum Sample in Relation
to Difference in Feeding Time

| Feeding Time | Reproducibility |
| --- | --- |
| 4 seconds | 2.1% |
| 10 seconds | 2.0% |

Calculation of the reproducibility is exactly same as that described in conjunction with Example 1.

EXAMPLE 3

The sensor for detecting lactic acid was mounted on the measuring cell. The liquid sample of 4 $\mu$l (or 10 $\mu$l) was injected into the metering section having a volume of 100 $\mu$l. The feeding pump was operated for 4 seconds (feeding rate of 0.1 ml/s). In this condition, lactic acid in the serum sample was repeatedly measured fifteen times. As a result, reproducibility after repetition is obtained as shown in Table 3.

TABLE 3

Reproducibility in Measurement of
Lactic Acid in Serum Sample in Relation to
Difference in Amount of Serum Sample Injected

| Amount Injected | Reproducibility |
| --- | --- |
| 4 $\mu$l | 2.1% |
| 10 $\mu$l | 2.2% |

Calculation of the reproducibility is exactly same as that described in conjunction with Example 1.

EXAMPLE 4

The sensor for detecting lactic acid was mounted on the measuring cell. The liquid sample of 4 $\mu$l was injected into the metering section having a volume of 100 $\mu$l. The feeding pump was operated at a feeding rate of 0.1 ml/s (or 0.3 ml/s) (feeding time of 4 seconds). In this condition, lactic acid in the serum sample was repeatedly measured fifteen times. As a result, reproducibility after repetition is obtained as shown in Table 4.

TABLE 4

Reproducibility in Measurement of
Lactic Acid in Serum Sample in Relation to
Difference in Feeding Rate by Pump

| Feeding rate | Reproducibility |
| --- | --- |
| 0.1 ml/s | 2.0% |
| 0.3 ml/s | 1.9% |

Calculation of the reproducibility is exactly same as that described in conjunction with Example 1.

EXAMPLE 5

The sensor for detecting lactic acid was mounted on the measuring cell. The liquid sample of 4 $\mu$l was injected into the metering sections having a volume of 50 μl (or 100 μl). The feeding pump was operated at a feeding rate of 0.1. ml/s (feeding time of 4 seconds). In this condition, lactic acid in the serum sample was repeatedly measured fifteen times. As a result, reproducibility after repetition is obtained as shown in Table 5.

TABLE 5

Reproducibility in Measurement of Lactic Acid in Serum Sample in Relation to Difference in Volume of Metering Portion

| Volume | Reproducibility |
|---|---|
| 50 μl | 3.1% |
| 100 μl | 2.1% |

Calculation of the reproducibility is exactly same as that described in conjunction with Example 1.

Figure 8:
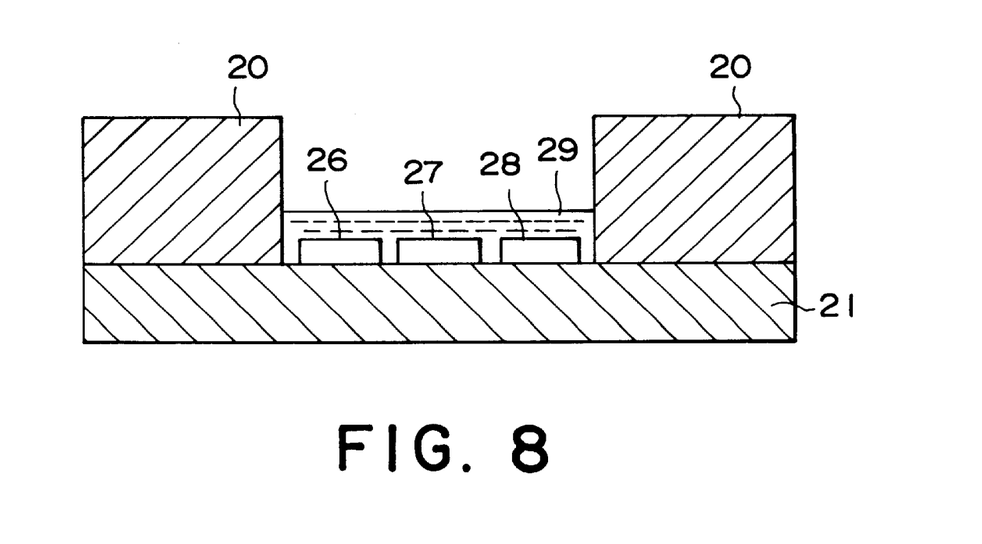
FIG. 8 is a sectional view of a sensor according to a second embodiment of this invention.

Now, description will proceed to a second embodiment of this invention. The second embodiment is basically similar in structure to the first embodiment except that the sensor 15 is replaced by a sensor 15' and that the O-ring 16 and the reference electrode 8 are omitted. In the following, the sensor 15' alone will be described.

Referring to FIG. 8, the sensor 15' comprises a reference electrode 26, a working electrode 27, and a counter electrode 28 formed on an insulating support substrate 21. An enzyme membrane 29 is deposited over the reference electrode 26, the working electrode 27, and the counter electrode 28. A photoresist layer 20 is deposited on opposite sides of the enzyme membrane 29 to a thickness greater than that of the enzyme membrane 29. In this embodiment, the O-ring 16 between the metering section 12 and the sensor 15 in the first embodiment can be omitted. Instead of the O-ring 16, the photoresist layer 20 composed of photosensitive insulating resin is formed. The sensor is coupled with the measuring cell 11 with the photoresist layer 20 tightly attached to the metering section 12. Thus, it is possible to avoid damage of the enzyme membrane 29 and leakage of the liquid. In addition, the reference electrode 8 separately arranged in the first embodiment is no longer required. Therefore, the apparatus can further be simplified in structure and reduced in production cost.

Next referring to FIG. 9, a third embodiment of this invention will be described. The third embodiment is basically similar in structure to the first embodiment except that the feeding pump 9 and the discharge pump 10 are replaced by a single pump 25. In the following, the pump 25 and the relevant part alone will be described.

Figure 9:
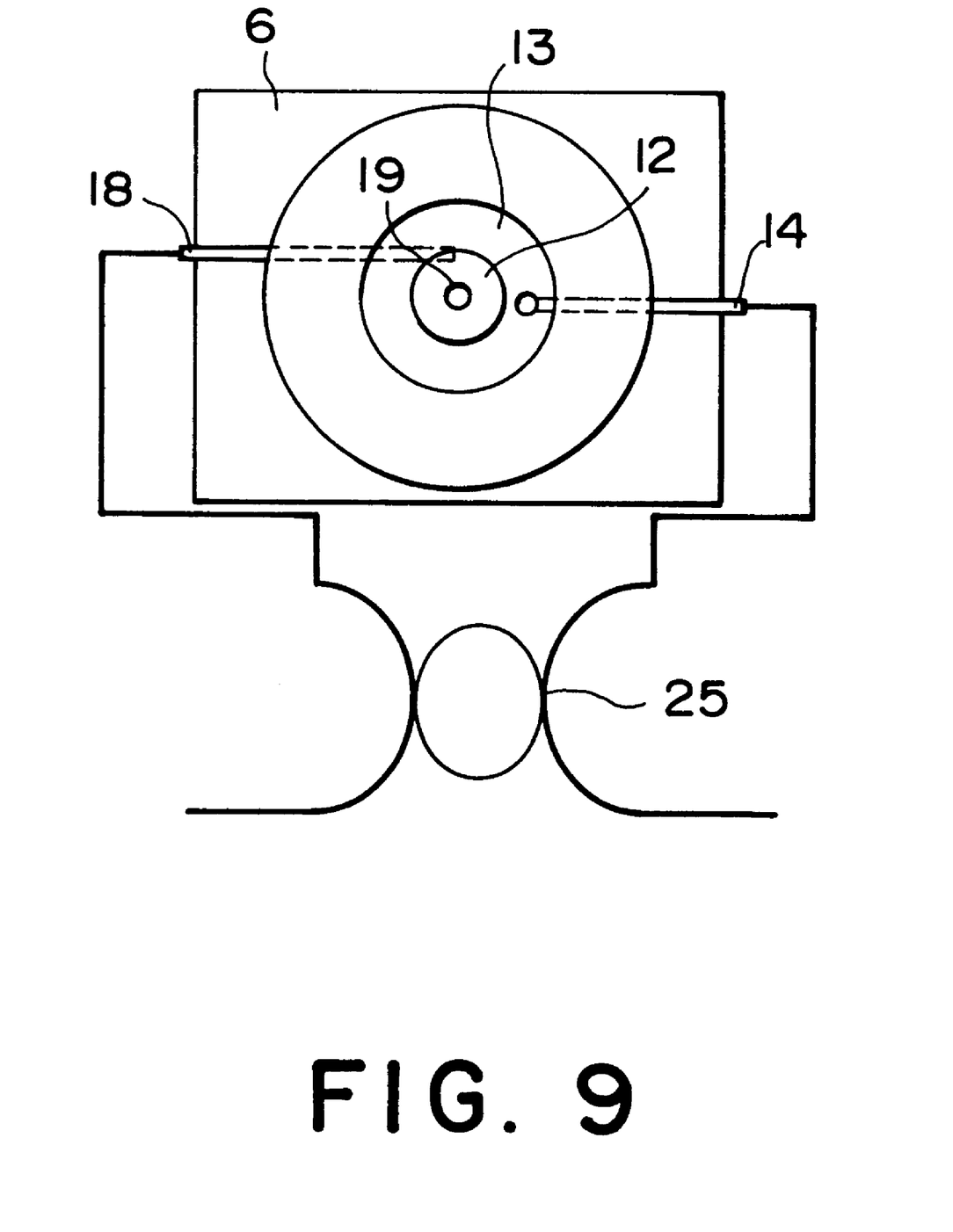
FIG. 9 is a plan view of a measuring cell according to a third embodiment of this invention.

As illustrated in FIG. 9, an injection side of the tube 4 between the buffer tank 5 and the buffer injection port 18 and a discharge side of the tube 4 between the buffer discharge port 14 and the waste tank 7 are arranged on opposite sides of the pump 25. In this arrangement, feeding and discharging operations of the buffer solution 22 to and from the measuring cell 11 can be carried out by the single pump 25. This is because squeezing directions of the pump 25 of the feeding and the discharging operations are reverse to each other. However, in this embodiment, the tube 4 must have a greater diameter at the injection side than at the discharge side. This is because variation in diameter of the tube 4 brings about the difference between the feeding rate and the discharge rate of the buffer solution 22.

As described above, the liquid sample is injected into the measuring cell through the sample injection port located at the upper part of the metering section. The buffer solution is automatically metered by simply operating the feeding and the discharging pumps without requiring a metering pump. Therefore, the measuring cell is simplified in structure so that the apparatus is manufactured at a low cost.

Since no complicated switching valve is required, miniaturization of the apparatus is achieved so that no restriction is imposed upon the portability and the measuring site.

The sensor can be exchanged not alone but together with the measuring cell. Thus, handling is easy.

Even if impurities and bubbles contained in the liquid sample enter into the measuring cell, such undesired substance can quickly be expelled through the sample injection port to the reservoir. Thus, the accuracy of measurement is remarkably improved.

What is claimed is:

1. A liquid component measuring apparatus comprising a measuring cell which measures a specific component of a predetermined amount of liquid sample by diluting, as diluted liquid sample, said predetermined amount of liquid sample with a buffer solution having a pH buffer capacity and a support electrolyte, said measuring cell comprising:

a metering section having an upper part tapered upward and having a metering space therein;

a sample injection port formed at a top of said upper part;

a buffer injection port coupled to said metering section for supplying said buffer solution to said metering space so that said metering space is completely filled with said buffer solution;

a reservoir disposed around said metering section for temporarily reserving, as a reserved buffer solution, the buffer solution which overflows from said sample injection port when said buffer solution is supplied to said metering space by said buffer injection port to be completely filled into said metering space and when said predetermined amount of liquid sample is introduced into said metering space from said buffer injection port so that said metering space is filled with said diluted liquid sample;

a stirrer disposed in said metering space for stirring said diluted liquid sample;

a sensor disposed in said metering space for sensing said specific component in said diluted liquid sample; and a buffer discharge port coupled to said reservoir for discharging said reserved buffer solution from said reservoir into the outside of said measuring cell.

2. A liquid component measuring apparatus as claimed in claim 1, wherein said upper part of the metering section has a conical outer surface.

3. A liquid component measuring apparatus as claimed in claim 2, wherein the conical outer surface of said upper part of the metering section has an inclination angle between 60° and 120°.

4. A liquid component measuring apparatus as claimed in claim 1, wherein at least a portion of said metering section that is brought into contact with said buffer solution and said diluted liquid sample is composed of a material selected from the group consisting of metal oxide, anti-corrosion metal, and hydrophobic macromolecule.

5. A liquid component measuring apparatus as claimed in claim 1, wherein at least a portion of said metering section that is brought into contact with said buffer solution and said diluted liquid sample is composed of stainless steel.

6. A liquid component measuring apparatus as claimed in claim 1, wherein at least a portion of said metering section that is brought into contact with said buffer solution and said diluted liquid sample is composed of a material selected from the group consisting of fluorine macromolecule and polyalkylsiloxane.

7. A liquid component measuring apparatus as claimed in claim 3, wherein at least a portion of said metering section that is brought into contact with said buffer solution and said diluted liquid sample has a first part composed of stainless steel and a second part composed of a material selected from the group consisting of fluorine macromolecule and polyalkylsiloxane.

8. A liquid component measuring apparatus as claimed in claim 1, wherein said sensor is mounted through an O-ring over a bottom of said metering section.

9. A liquid component measuring apparatus as claimed in claim 1, wherein said sensor comprises a working electrode, and a counter electrode formed on an insulating support substrate, an enzyme membrane formed on said working and said counter electrodes, and a resin layer surrounding said enzyme membrane.

10. A liquid component measuring apparatus as claimed in claim 1, wherein said apparatus further comprises a single pump for feeding said buffer solution to said buffer injection port and for discharging said reserved buffer solution from said reservoir into the outside of said measuring cell, wherein said pump has a greater diameter fitting at the injection side than at the discharge side.

* * * * *